(12) United States Patent
Hu

(10) Patent No.: US 9,593,076 B2
(45) Date of Patent: Mar. 14, 2017

(54) CYCLIC PROCESS FOR PRODUCING TAURINE

(71) Applicant: VITAWORKS IP, LLC, North Brunswick, NJ (US)

(72) Inventor: Songzhou Hu, Princeton, NJ (US)

(73) Assignee: Vitaworks IP, LLC, North Brunswick, NJ (US)

(*) Notice: Subject to any disclaimer, the term of this patent is extended or adjusted under 35 U.S.C. 154(b) by 0 days.

(21) Appl. No.: 15/238,621

(22) Filed: Aug. 16, 2016

(65) Prior Publication Data

US 2016/0355470 A1    Dec. 8, 2016

Related U.S. Application Data

(63) Continuation-in-part of application No. 14/120,651, filed on Jun. 12, 2014, now Pat. No. 9,428,451, which is a continuation-in-part of application No. 14/120,046, filed on Apr. 18, 2014, now Pat. No. 9,428,450.

(51) Int. Cl.
C07C 303/02    (2006.01)

(52) U.S. Cl.
CPC ................... C07C 303/02 (2013.01)

(58) Field of Classification Search
None
See application file for complete search history.

(56) References Cited

U.S. PATENT DOCUMENTS

| | | |
|---|---|---|
| 1,932,907 A | 10/1933 | Otto |
| 1,999,614 A | 4/1935 | Otto et al. |
| 2,820,818 A | 1/1958 | Sexton |
| 2014/0121405 A1* | 5/2014 | Chen ............... C07C 303/18 562/104 |
| 2015/0210633 A1 | 7/2015 | Hu |

FOREIGN PATENT DOCUMENTS

| | | |
|---|---|---|
| CN | 101486669 A | 7/2009 |
| CN | 101508657 A | 8/2009 |
| CN | 101508658 A | 8/2009 |
| CN | 101508659 A | 8/2009 |
| DE | 219023 A3 | 2/1985 |
| WO | 0177071 A1 | 10/2001 |

OTHER PUBLICATIONS

International Search Report for corresponding International Application No. PCT/CN2015/000232, mailed Jul. 1, 2015.
USPTO Non-Final Office Action for corresponding U.S. Appl. No. 15/228,568 dated Oct. 5, 2016.
USPTO Non-Final Office Action for corresponding U.S. Appl. No. 15/228,539 dated Oct. 17, 2016.

* cited by examiner

*Primary Examiner* — Karl J Puttlitz
(74) *Attorney, Agent, or Firm* — Graham Curtin, P.A.

(57) ABSTRACT

There is disclosed a process for producing taurine by the ammonolysis of alkali isethionate in the presence of alkali ditaurinate or alkali tritaurinate, or their mixture, to inhibit the formation of byproducts and to continuously convert the byproducts of the ammonolysis reaction to alkali taurinate. Alkali taurinate is neutralized with isethionic acid to obtain taurine and to regenerate alkali isethionate. The production yield is increased to from 90% to nearly quantitative. The ammonolysis reaction is catalyzed by alkali salts of hydroxide, sulfate, sulfite, phosphate, or carbonate.

6 Claims, 1 Drawing Sheet

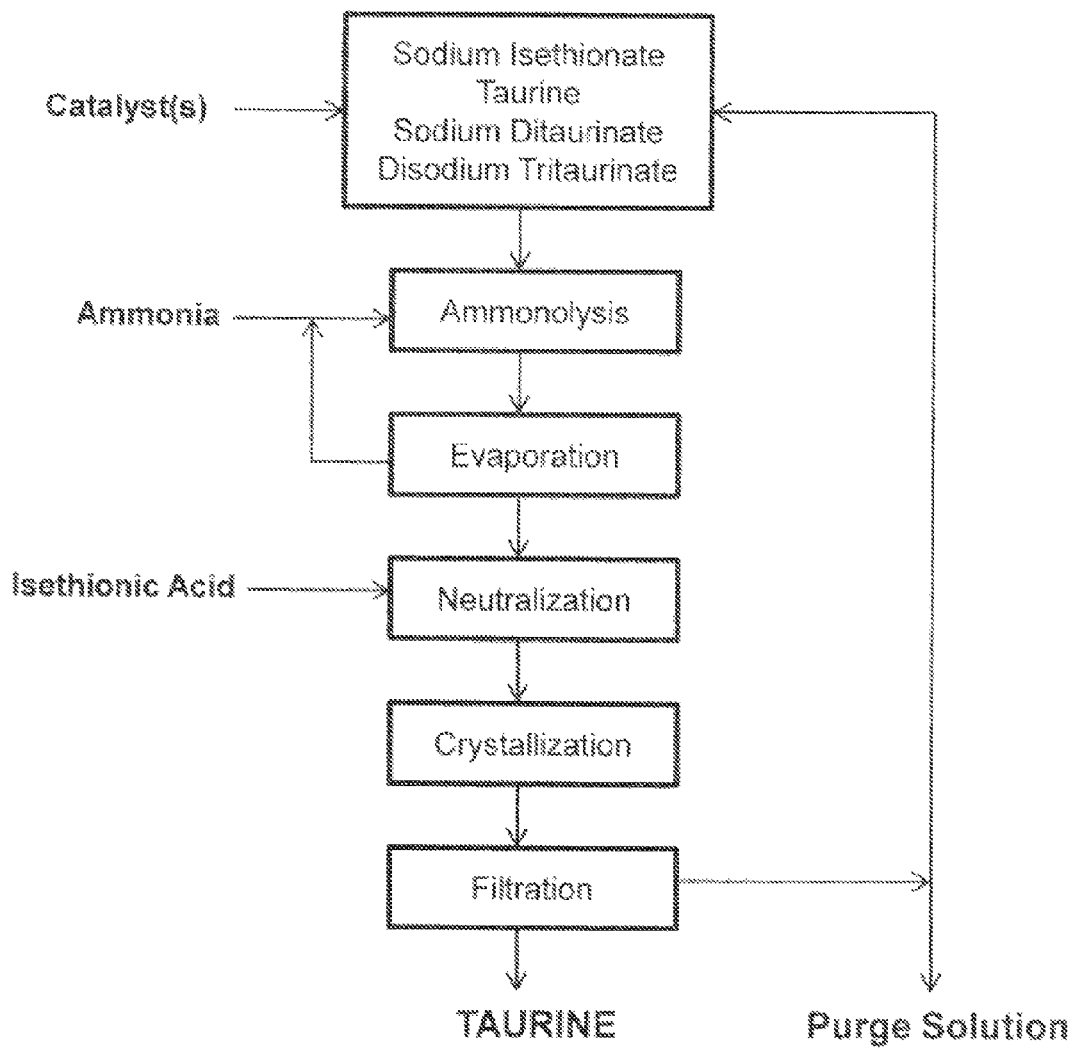

CYCLIC PROCESS FOR PRODUCING TAURINE

CROSS REFERENCE TO RELATED APPLICATIONS

This application is a continuation-in-part of application Ser. No. 14/120,651, filed on Jun. 12, 2014, which is a continuation-in-part of application Ser. No. 14/120,046, filed on Apr. 18, 2014, both of which are incorporated here by reference.

TECHNICAL FIELD

The present invention relates to a cyclic process for the production of taurine from alkali isethionate in a high overall yield (i.e., greater than 90% to nearly quantitative) by carrying out the ammonolysis reaction of alkali isethionate to alkali taurinate in the presence of a mixture of alkali ditaurinate and alkali tritaurinate, followed by neutralization with isethionic acid.

BACKGROUND OF THE INVENTION

Taurine can be referred to as 2-aminoethanesulfonic acid and is one of the amino sulfonic acids found in the tissues of many animals. Taurine is an extremely useful compound with beneficial pharmacological effects, such as detoxification, fatigue-relief, and nourishing and tonifying effects. As a result, taurine finds wide applications as an essential ingredient for human and animal nutrition.

Taurine is currently produced in an amount of over 50,000 tons per year from either ethylene oxide or monoethanolamine. At the present time, most taurine is produced from ethylene oxide, following a three-step process: (1) the addition reaction of ethylene oxide with sodium bisulfate to yield sodium isethionate; (2) the ammonolysis of sodium isethionate to yield sodium taurinate; (3) the neutralization with an acid, i.e., hydrochloric acid and preferably, sulfuric acid, to generate taurine and inorganic salts.

Although the ethylene oxide process is well established and widely practiced in commercial production, the overall yield is not very high, less than 80%. Moreover, the process generates a large waste stream that is increasingly difficult to dispose of.

The first stage of the ethylene oxide process, the addition reaction of ethylene oxide with sodium bisulfite, is known to yield sodium isethionate in high yield, practically quantitative, as disclosed in U.S. Pat. No. 2,820,818 under described conditions.

Therefore, the problems encountered in the production of taurine from the ethylene oxide process arise from the ammonolysis of sodium isethionate and from the separation of taurine from sodium sulfate.

U.S. Pat. No. 1,932,907 discloses that sodium taurinate is obtained in a yield of 80%, when sodium isethionate undergoes ammonolysis reaction in a molar ratio of 1:6.8 for 2 hrs at 240 to 250° C. U.S. Pat. No. 1,999,614 describes the use of catalysts, i.e., sodium sulfate, sodium sulfite, and sodium carbonate, in the ammonolysis reaction. A mixture of sodium taurinate and sodium ditaurinate is obtained in a yield as high as 97%. However, the percentage for sodium taurinate and sodium ditaurinate in the mixture is not specified.

DD219023 describes detailed results on the product distribution of the ammonolysis reaction of sodium isethionate. When sodium isethionate undergoes the ammonolysis reaction with 25% aqueous ammonia in a molar ratio of 1:9 at about 280° C. for 45 minutes in the presence of sodium sulfate and sodium hydroxide as catalyst, the reaction products comprise 71% of sodium taurinate and 29% of sodium di- and tri-taurinate.

WO01/77071 is directed to a process for the preparation of ditaurine by heating an aqueous solution of sodium taurinate at a temperature of 210° C. in the presence of a reaction medium. A mixture of sodium taurinate and sodium ditaurinate is obtained.

It is therefore concluded from the foregoing references that the ammonolysis of sodium isethionate invariably yields a mixture of sodium taurinate, sodium ditaurinate, and sodium tritaurinate. The percentage yield of sodium taurinate has not been more than 80%.

In order to obtain taurine from sodium taurinate, U.S. Pat. No. 2,693,488 discloses a method of using ion exchange resins involving a strongly acid ion exchange resin in hydrogen form, and then an anion exchange resin in basic form. This process is complicated and requires the use of a large quantity of acid and base to regenerate the ion exchange resins in each production cycle.

On the other hand, CN101508657, CN101508658, CN101508659, and CN101486669 describe a method of using sulfuric acid to neutralize sodium taurinate to obtain a solution of taurine and sodium sulfate. Crude taurine is easily obtained by filtration from a crystalline suspension of taurine after cooling. However, the waste mother liquor still contains taurine, sodium sulfate, and other unspecified organic impurities, which are identified as a mixture of sodium ditaurinate and sodium tritaurinate.

In the co-pending application Ser. No. 14/120,046, a novel process is disclosed for converting alkali ditaurinate or alkali tritaurinate, or their mixture, to alkali taurinate.

U.S. Pat. No. 8,609,890 discloses a process of using isethionic acid or sulfur dioxide to neutralize alkali taurinate to producing taurine and to regenerate alkali isethionate. U.S. Pat. No. 9,108,907 further discloses a process of using isethionic acid prepared from ethanol to neutralize alkali taurinate to regenerate alkali isethionate. The aim is to reduce or eliminate the use of sulfuric acid as an acid agent in the production of taurine. However, the production yield remains low, due to the accumulation of impurities, which have now been identified as alkali ditaurinate and alkali tritaurinate.

It is, therefore, an object of the present invention to disclose a process for the production of taurine from alkali isethionate in a high overall yield (i.e., greater than 90% to nearly quantitative). According to the process of the present invention, a solution of alkali isethionate or regenerated alkali isethionate, alkali ditaurinate, and alkali tritaurinate is mixed with an excess ammonia and is subjected continuously to the ammonolysis reaction to form a mixture of alkali taurinate, alkali ditaurinate, and alkali tritaurinate, in the presence of one or more catalysts. After removal of excess ammonia, isethionic acid is used to neutralize the alkaline solution to yield taurine and to regenerate alkali isethionate.

The advantage of using isethionic acid as an acid becomes apparent in that no isolation of alkali salt is necessary after separation of crystalline taurine from the mother liquor containing alkali isethionate, alkali ditaurinate, and alkali tritaurinate.

DESCRIPTION OF THE INVENTION

The present invention relates to a process for the production of taurine by the ammonolysis reaction of alkali isethionate in the presence of alkali ditaurinate and alkali tritaurinate to inhibit the formation of byproducts, to increase the production yield, and to greatly reduce the waste discharge from the production process.

The present invention further relates to a process for producing taurine by neutralizing alkali taurinate with isethionic acid to regenerate alkali isethionate. The alkali metals are lithium, sodium, or potassium.

The process according to the present invention starts with mixing a solution of alkali isethionate or regenerated alkali isethionate, alkali ditaurinate, and alkali tritaurinate, with an excess of ammonia. The ammonolysis is carried out at a temperature from 160° C. to 260° C. under the pressure from autogenous to 260 bars for 1 to 6 hours.

After the ammonolysis reaction, excess ammonia is dispelled from the reaction solution and reclaimed for reuse. A solution of alkali taurinate is obtained, along with alkali ditaurinate, alkali tritaurinate, and a trace amount of unreacted alkali isethionate.

The strongly basic solution is neutralized with isethionic acid to pH 5-9 to yield a crystalline suspension of taurine in a solution of alkali isethionate, alkali ditaurinate, alkali tritaurinate, and a small amount of unreacted alkali isethionate. The initial suspension is optionally concentrated, then cooled to crystallize taurine. Taurine is obtained by means of solid-liquid separation.

After separation of taurine, the mother liquor, containing regenerated alkali isethionate, alkali ditaurinate, and alkali tritaurinate, is saturated with ammonia and is subjected to the ammonolysis reaction.

Useful and effective catalysts are found among the alkali salts of hydroxide, carbonate, bicarbonate, hydrogen sulfate, sulfate, bisulfite, sulfite, nitrate, phosphate, chlorate, and perchlorate. Such salts are sodium hydroxide, lithium hydroxide, potassium hydroxide, lithium carbonate, lithium bicarbonate, sodium bicarbonate, sodium bicarbonate, potassium bicarbonate, lithium carbonate, sodium carbonate, potassium carbonate, lithium sulfate, sodium sulfate, potassium sulfate, lithium phosphate, sodium phosphate, potassium phosphate, lithium sulfite, sodium sulfite, and potassium sulfite.

The catalyst for the ammonolysis reaction of alkali isethionate in the presence of alkali ditaurinate and alkali tritaurinate can be one component or a combination of two or more components. Preferable catalysts are alkali hydroxide and the most preferable catalyst is sodium hydroxide.

The amount of the catalyst used is not limited, but is usually from 0.01 to 10 in molar ratio of the catalyst to alkali isethionate. The ratio is preferably in the range of 0.01 to 1, more preferably 0.1 to 0.5, most preferably 0.2 to 0.3. A suitable amount of catalyst can be selected by those skilled in the art for the ammonolysis reaction to complete in desired time.

The acid used in the neutralization process is judicially chosen to be isethionic acid, which can be obtained from alkali isethionate, ethylene oxide, or ethanol by methods known in prior arts. A particularly suitable method for producing isethionic acid is utilizing bipolar membrane electrodialysis of alkali isethionate to yield isethionic acid and alkali hydroxide.

The cyclic process according to the present invention affords taurine in a yield of greater than 90%, to nearly quantitative, and generates no waste other than a small amount of purge from the cyclic system.

The process according to the present invention can be carried out discontinuously, semi-continuously, and continuously.

BRIEF DESCRIPTION OF THE DRAWING

FIG. 1 illustrates one embodiment of a flowchart for producing taurine from alkali isethionate using isethionic acid as neutralization agent.

EXAMPLES

The following examples illustrate the practice of this invention but are not intended to limit its scope.

Example 1

To a 2-L autoclave are added 1200 mL of 24% ammonia solution, 296 g of sodium isethionate, and 2 g of sodium hydroxide. The solution is heated to 260° C. for 2 hours under autogenous pressure. After removal of ammonia, 252 g of isethionic acid is used to bring the pH of the solution to pH 8. A suspension of crystalline taurine is obtained. After cooling to room temperature under slow stirring, taurine is recovered by filtration and dried to 188.6 g. Taurine is recovered in a yield of 75.4%.

Example 2

To the mother liquor of Example 1 is added 340 g of gaseous ammonia and total volume is adjusted to 1500 mL with deionized water, followed by addition of 10.5 g of sodium hydroxide. The solution is placed in a 2-L autoclave and is subjected to ammonolysis reaction and treatment with isethionic acid as described in Example 1.

Taurine, 234.9 g after drying, is obtained in a yield of 93.1% on the basis of used isethionic acid.

The mother liquor after isolation of taurine, after being saturated with ammonia, is repeatedly subjected to the ammonolysis reaction in the presence of 15 g of sodium hydroxide 5 times for an overall yield of taurine of 96.4% on the basis of isethionic acid used.

Example 3

This set of examples shows the effect of a different catalyst on the ammonolysis of regenerated sodium isethionate in the presence of a mixture of sodium ditaurinate and sodium tritaurinate obtained from the mother liquor of taurine crystallization.

All examples are for 0.05 mole of sodium isethionate, present in the mother liquor, dissolved in 35 mL of 20% aqueous ammonia solution in a molar ratio of 1:8 for sodium isethionate to ammonia. Calculated amount of catalyst are added to the solution. The ratio of (di+tritaurinate)/isethionate in the mother liquor is 0.3. The ammonolysis reaction is carried out in an 100 mL autoclave at 220° C. under autogenous pressure for two hours. The content of taurine, ditaurine, and tritaurine is assayed by HPLC analysis. The yields are calculated according to the following formula:

Taurinate Yield (%)=[Taurine]/[Sodium Isethionate]

TABLE

Effect of Catalyst on Ammonolysis of Sodium Isethionate in the Presence of a Mixture of Sodium Ditaurinate and Sodium Tritaurinate

| Ex | Catalyst | Catalyst/ Isethionate (ratio by weight) | Taurinate (molar yield %) |
|---|---|---|---|
| 1 | None | 0 | 55 |
| 2 | Sodium carbonate | 0.15 | 97 |
| 3 | Sodium sulfite | 0.15 | 96 |
| 4 | Potassium hydroxide | 0.10 | 97 |
| 5 | Potassium carbonate | 0.15 | 96 |
| 6 | Potassium sulfite | 0.10 | 97 |
| 7 | Lithium hydroxide | 0.10 | 95 |
| 8 | Lithium carbonate | 0.10 | 93 |

TABLE-continued

Effect of Catalyst on Ammonolysis of Sodium Isethionate in the Presence of a Mixture of Sodium Ditaurinate and Sodium Tritaurinate

| Ex | Catalyst | Catalyst/ Isethionate (ratio by weight) | Taurinate (molar yield %) |
|---|---|---|---|
| 9 | Sodium phosphate | 0.15 | 97 |
| 10 | Potassium phosphate | 0.15 | 95 |
| 11 | Sodium sulfate | 0.50 | 85 |
| 12 | Potassium acetate | 0.20 | 94 |
| 13 | Sodium acetate | 0.20 | 94 |

It will be understood that the foregoing examples, drawing, and explanation are for illustrative purposes only and that various modifications of the present invention will be self-evident to those skilled in the art. Such modifications are to be included within the spirit and purview of this application and the scope of the appended claims.

What is claimed is:

1. A cyclic process for producing taurine from alkali isethionate, comprising:
   (a) adding one or a combination of two or more catalysts to an ammonia solution of a mixture of alkali isethionate, alkali ditaurinate, and alkali tritaurinate, and subjecting the solution of to ammonolysis reaction to yield a mixture of alkali taurinate, alkali ditaurinate, and alkali tritaurinate;
   (b) removing excess ammonia and neutralizing with isethionic acid to obtain a crystalline suspension of taurine in a solution of alkali isethionate, alkali ditaurinate, and alkali tritaurinate;
   (c) separating taurine by means of solid-liquid separation; and
   (d) returning the mother liquor of (c) to step (a) for further ammonolysis.

2. The process according to claim 1, wherein one or a combination of two or more catalysts for the ammonolysis reaction is selected from alkali salts of hydroxide, carbonate, sulfate, sulfite, phosphate, nitrate, or carboxylate.

3. The process according to claim 1, wherein the production yield of taurine is greater than 85%.

4. The process according to claim 1, wherein the production yield of taurine is greater than 90%.

5. The process according to claim 1, wherein the production yield of taurine is greater than 95%, to nearly quantitative.

6. The process according to claim 1, wherein the alkali metals are lithium, sodium, or potassium.

* * * * *